US00PP14897P2

(12) United States Plant Patent
Jensen

(10) Patent No.: US PP14,897 P2
(45) Date of Patent: Jun. 15, 2004

(54) CAMPANULA PLANT NAMED '10.00.99'

(50) Latin Name: *Campanula×haylodgensis*
Varietal Denomination: 10.00.99

(75) Inventor: Gert K. Jensen, Odense N (DK)

(73) Assignee: Gartneriet PKM ApS, Odense (DK)

( * ) Notice: Subject to any disclaimer, the term of this patent is extended or adjusted under 35 U.S.C. 154(b) by 79 days.

(21) Appl. No.: 10/396,533

(22) Filed: Mar. 25, 2003

(51) Int. Cl.[7] ..... A01H 5/00
(52) U.S. Cl. ..... Plt./263
(58) Field of Search ..... Plt./263

*Primary Examiner*—Kent Bell
(74) *Attorney, Agent, or Firm*—C. A. Whealy

(57) ABSTRACT

A distinct cultivar of Campanula plant named '10.00.99', characterized by its upright and outwardly spreading growth habit; single violet blue campanulate flowers; and temperature tolerant from −15 to 35° C.

2 Drawing Sheets

Botanical classification/cultivar designation: *Campanula×haylodgensis* cultivar 10.00.99.

BACKGROUND OF THE INVENTION

The present Invention relates to a new and distinct cultivar of Campanula plant, botanically known as *Campanula× haylodgensis*, and hereinafter referred to by the name '10.00.99'.

The new Campanula is a naturally-occurring branch mutation of an unidentified selection of *Campanula× haylodgensis,* not patented. The cultivar 10.00.99 was discovered and selected by the Inventor from within a population of plants of the unidentified selection of *Campanula× haylodgensis* in a controlled environment in March, 2000, in Odense, Denmark.

Asexual reproduction of the new cultivar by cuttings taken at Odense, Denmark, since March, 2000, has shown that the unique features of this new Campanula are stable and reproduced true to type in successive generations.

SUMMARY OF THE INVENTION

Plants of the cultivar 10.00.99 have not been observed under all possible environmental conditions. The phenotype may vary somewhat with variations in environment such as temperature and/or light intensity without, however, any variance in genotype.

The following traits have been repeatedly observed and are determined to be the unique characteristics of '10.00.99'. These characteristics in combination distinguish '10.00.99' as a new and distinct cultivar:

1. Upright and outwardly spreading growth habit.
2. Single violet blue campanulate flowers.
3. Temperature tolerant from −15 to 35° C.

Plants of the new Campanula are most similar to plants of the parent, the unidentified selection of *Campanula× haylodgensis*. Plants of the new Campanula differ from plants of the parent selection in the following characteristics:

1. Plants of the new Campanula were more freely flowering than plants of the parent selection.
2. Plants of the new Campanula had single flowers whereas plants of the parent selection had double flowers.

BRIEF DESCRIPTION OF THE PHOTOGRAPHS

The accompanying colored photographs illustrate the overall appearance of the new cultivar, showing the colors as true as it is reasonably possible to obtain in colored reproductions of this type. Colors in the photographs may differ from the color values cited in the detailed botanical description which accurately describe the colors of the new Campanula.

The photograph on the first sheet comprises a side perspective view of a typical plant of '10.00.99'.

The photograph on the second sheet comprises a close-up view of typical flowering stems of '10.00.99'.

DETAILED BOTANICAL DESCRIPTION

In the following description, color references are made to The Royal Horticultural Society Colour Chart, 2001 Edition, except where general terms of ordinary dictionary significance are used. Plants used for the above-mentioned photographs and botanical description were grown in Odense, Denmark in 6-cm containers in a glass-covered greenhouse. During the production of the plants, day temperatures were about 18 to 20° C., night temperatures were about 16 to 18° C., and light levels were about 25 W/m$^2$. Plants used were about 12 weeks old when the photographs and description were taken.

Botanical classification: *Campanula×haylodgensis* cultivar 10.00.99.

Parentage: Naturally-occurring branch mutation of an unidentified selection of *Campanula×haylodgensis*, not patented.

Propagation:

*Type.*—By cuttings.

*Time to initiate roots.*—About 16 to 18 days at 16 to 18° C.

*Root description.*—Fibrous, fine; white in color.

Plant description:

*Form.*—Upright and outwardly spreading; rounded inverted triangle.

*Plant height, soil level to top of plant plane.*—About 20 cm.

*Plant width.*—About 20 cm.

*Lateral branch description.*—Quantity: About 30 per plant. Length: About 20 cm. Texture: Smooth, glabrous. Color: 136A.

*Foliage description.*—Arrangement: Alternate, simple. Quantity per lateral branch: About 12 to 14. Length: About 1.4 cm. Width: About 1.4 cm. Shape: Ovate to cordate. Apex: Acuminate. Base: Obtuse. Margin: Serrate. Texture, upper and lower surfaces: Smooth, glabrous. Venation pattern: Pinnate. Color: Developing foliage, upper surface: 144B. Developing foliage, lower surface: 144C. Fully expanded foliage, upper and lower surfaces: 136A. Venation, upper and lower surfaces: 144A. Petiole: Length: About 1.5 cm. Diameter: About 0.5 mm. Texture, upper and lower surfaces: Smooth; glabrous. Color, upper and lower surfaces: 144A.

Flower description:

*Flower type and habit.*—Single campanulate flowers arranged in terminal panicles. Flowers face mostly upright. Flowers persistent.

*Fragrance.*—Pungent.

*Natural flowering season.*—Continuously flowering throughout the year if exposed to short (less than 11 hours of dark) nyctoperiods.

*Quantity.*—Freely flowering with about six flowers and flower buds per lateral branch.

*Flower longevity on the plant.*—About 22 days.

*Flower diameter.*—About 2.2 cm.

*Flower depth (height).*—About 1.2 cm.

*Flower buds.*—Length: About 1 cm. Diameter: About 2 mm. Shape: Oblong. Color: 91A.

*Petals.*—Quantity per flower: About five. Length: About 5 mm. Width: About 8 mm. Shape: Roughly ovate. Apex: Acute. Margin: Entire. Texture, upper and lower surfaces: Smooth; glabrous; velvety. Color: Upper and lower surfaces, when opening: 91A to 91C. Upper and lower surfaces, fully opened: 91B to 91D.

*Sepals.*—Quantity per flower: About five. Length: About 3 mm. Diameter: About 1 mm. Shape: Narrowly deltoid. Apex: Acute. Margin: Entire. Color, upper and lower surfaces: 138A.

*Peduncles.*—Length: About 7 mm. Diameter: About 0.2 mm. Strength: Weak. Color: 138A.

*Reproductive organs.*—Androecium: Stamens per flower: About five. Anther shape: Linear. Anther length: About 2 mm. Anther color: 16A. Pollen amount: Abundant. Pollen color: 16A. Gynoecium: Quantity of pistils per flower: One. Pistil length: About 1 cm. Stigma shape: Three-lobed. Stigma color: 11A. Style length: About 6 mm. Style color: 117D. Ovary color: 140D.

*Seeds.*—Quantity per flower: About five. Length: About 2 mm. Diameter: About 1 mm. Color: 140D.

Disease/pest resistance: Under commercial production conditions, plants of the new Campanula have not been noted to be resistant to pathogens or pests common to Campanula.

Temperature tolerance: Plants of the new Campanula have been observed to tolerate temperatures from −15 to 35° C. in Odense, Denmark.

It is claimed:

1. A new and distinct cultivar of Campanula plant named '10.00.99', as illustrated and described.

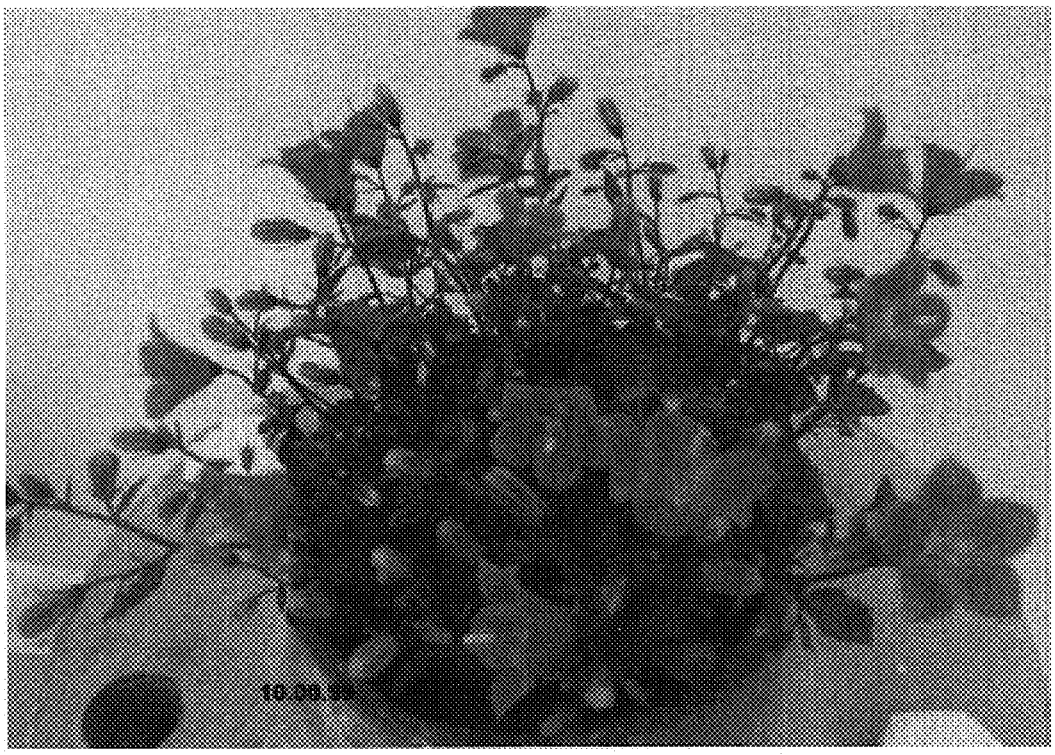

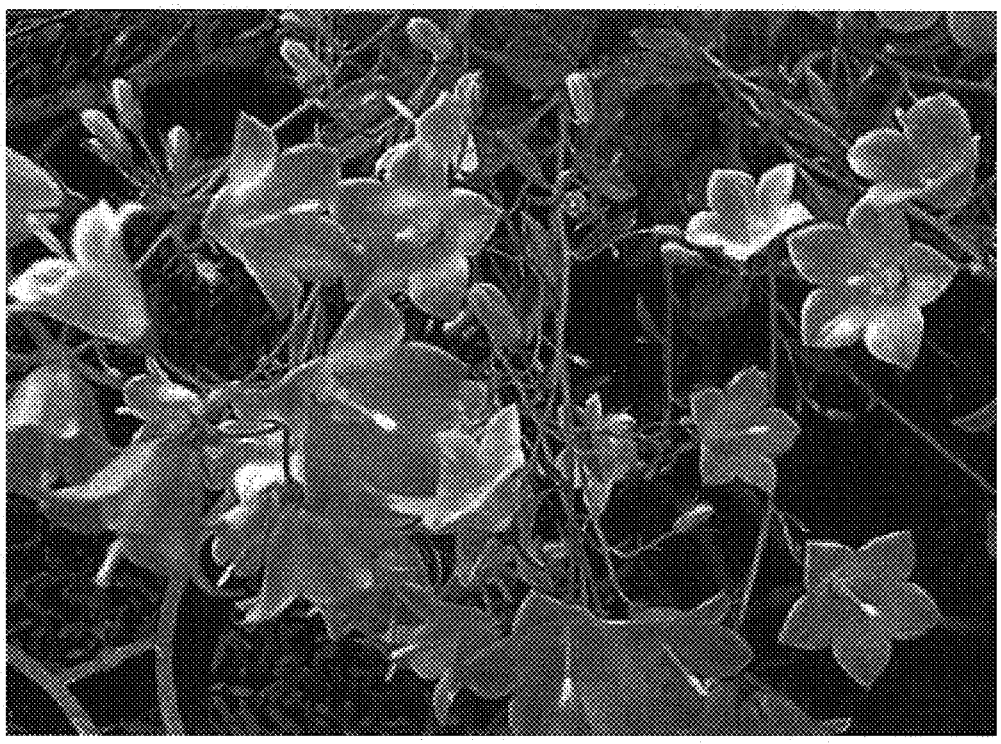

* * * * *